(12) United States Patent
Geliebter (10) Patent No.: US 7,718,166 B2
(45) Date of Patent: May 18, 2010

(54) IMMUNOTHERAPY FOR PROSTATE CANCER USING RECOMBINANT BACILLE CALMETTE-GUERIN EXPRESSING PROSTATE SPECIFIC ANTIGENS

(75) Inventor: Jan Geliebter, Brooklyn, NY (US)

(73) Assignee: Applied Immune Technologies, Scarsdale, NY (US)

( * ) Notice: Subject to any disclaimer, the term of this patent is extended or adjusted under 35 U.S.C. 154(b) by 1387 days.

(21) Appl. No.: 10/378,449

(22) Filed: Mar. 3, 2003

(65) Prior Publication Data

US 2004/0022770 A1 Feb. 5, 2004

Related U.S. Application Data

(60) Provisional application No. 60/360,839, filed on Mar. 1, 2002.

(51) Int. Cl.
 *C12N 1/21* (2006.01)
(52) U.S. Cl. .................. 424/93.46; 435/69.1; 435/69.3; 435/252.3; 435/252.31
(58) Field of Classification Search ...................... 514/2; 435/252.31; 530/350
 See application file for complete search history.

(56) References Cited

U.S. PATENT DOCUMENTS

| | | | |
|---|---|---|---|
| 5,776,465 A | | 7/1998 | O'Donell et al. |
| 5,830,475 A | * | 11/1998 | Aldovini et al. .......... 424/200.1 |
| 5,925,362 A | | 7/1999 | Spitler et al. |
| 6,387,888 B1 | * | 5/2002 | Mincheff et al. .............. 514/44 |
| 6,565,852 B1 | * | 5/2003 | Paterson .................. 424/200.1 |
| 2002/0160502 A1 | | 10/2002 | Chung et al. |

OTHER PUBLICATIONS

Schmittgen et al (Int J Cancer, 2003, 107:323-329).*
Grauer et al (Cancer Research, 1998, 58:4787-9).*
Zeoli et al (Proceedings of the American Association for Cancer Research, 2000, 41:875, abstract #5560, IDS).*
Zeoli et al (The Prostate Journal, Apr. 2001, vol. 3, p. 92-97).*
GenBank accession No. AF007544, Homo sapiens prostate-specific membrane antigen (PSMA), pp. 1-3 Only.*
Zeoli et al (Proceedings of the American Association for Cancer Research, Mar. 2001, 41:875, abstract #5560, IDS).*
O'Keefe et al (Biochemica et Biophysica Acta, 1998, 1443:113-127).*
NCBI sequence viewer "Accession # AAC83972," p. 1-2.*
BLAST search results for AAC83972, p. 1-8 only.*
NCBI sequence viewer "Accession # AAC83972" Dec. 9, 1998.*
BLAST search results for AAC83972, p. 1-8 only, Jul. 20, 2008.*
Geliebter et al., Expression of PSA in recombinant BCG: Potential for immunotherapy of prostate cancer. Proced. American Assoc. Cancer Res. Mar. 1997, vol. 38, p. 403.
Zeoli et al., Expression of prostate specific molecules in BCG: A potential immunotherapeutic vaccine, Proced. American Assoc. Cancer Res., Mar. 2000, vol. 41, p. 875.
Hwang et al., "Prostate Cancer Vaccines: Current Status," Seminars in Oncology, vol. 26, No. 2 (1999) pp. 192-201.
Simons et al., "Ex Vivo Gene Therapy Using Cytokine-Transduced Tumor Vaccines: Molecular and Clinical Pharmacology," Seminars in Oncology, vol. 25, No. 6 (1998) pp. 661-676.
Karr et al., "The Presence of Prostate-specific Antigen-related Genes in Primates and the Expression of Recombinant Human Prostate-specific Antigen in a Transfected Murine Cell Line," Cancer Research, vol. 55 (1995) pp. 2455-2462.
Maraj et al., "Prostate-specific membrane antigen," British Journal of Urology, vol. 81 (1998) pp. 523-528.
Stover et al., "New use of BCG for recombinant vaccines," Nature, vol. 351 (1991) pp. 456-460.
O'Donnell et al., "Recombinant Mycobacterium bovis BCG Secreting Functional Interleukin-2 Enhances Gamma Interferon Production by Splenocytes," Infection and Immunity, vol. 62, No. 6 (1994) pp. 2508-2514.

* cited by examiner

*Primary Examiner*—Laura B Goddard
(74) *Attorney, Agent, or Firm*—Kenyon & Kenyon LLP (57) ABSTRACT

The present invention relates to the treatment of prostate cancer. Methods and compositions comprising recombinant BCG are provided for eliciting potent immune responses against prostate specific antigens that are effective for treatment of prostate cancer and metastatic disease.

16 Claims, 5 Drawing Sheets

Lane    1    2    3    4    5    6    7    8

IMMUNOTHERAPY FOR PROSTATE CANCER USING RECOMBINANT BACILLE CALMETTE-GUERIN EXPRESSING PROSTATE SPECIFIC ANTIGENS

RELATED APPLICATIONS

This application claims the benefit of U.S. Ser. No. 60/360,839, filed Mar. 1, 2002, which is incorporated by reference.

FIELD OF THE INVENTION

The present invention relates to the treatment of prostate cancer. Methods and compositions comprising recombinant BCG are provided for eliciting potent immune responses against prostate specific antigens that are effective for treatment of prostate cancer and metastatic disease.

BACKGROUND OF THE INVENTION

Prostate cancer (CaP) is now the most common cancer in American men, with approximately 180,400 new cases estimated for the year 2000. In 1990, CaP surpassed lung cancer as the most commonly diagnosed cancer among American men. Approximately 189,000 cases, or thirty percent of all newly diagnosed cancers in American men in 2002 will be CaP. One in six American men will be diagnosed with CaP in his lifetime, and this cancer is the second leading cause of cancer deaths in American men with approximately 30,200 deaths estimated for the year 2002.

Ninety percent of CaP cases where the cancer is confined to the prostate (i.e., "organ-confined") can be cured with surgery if discovered early, but because there is no effective systemic therapy for this disease, the prognosis is poor once the tumor has spread beyond the gland itself and about half of the patients with CaP have clinically advanced (i.e., extraprostatic/extracapsular) disease at the time of initial diagnosis. Even in those patients initially determined to have organ-confined disease, one-third actually have undetected micrometastatic disease, as determined by subsequent pathological staging or disease progression. In all, more than 65% of patients with CaP develop metastatic disease.

Immunotherapy for the treatment of metastatic prostate cancer is based on the activation of the host's immune response against tumor-associated antigens (TAA) present on tumor cells that distinguish them from normal cells. TAA may be normal, tissue-specific cellular proteins that are upregulated on cancer cells, mutated proteins, oncofetal antigens, growth factor receptors, oncogene and tumor-suppressor gene products, among others.

Prostate cancer is an ideal candidate for immunotherapy for many reasons. There is a substantial failure rate of current therapies for the primary tumor and a lack of effective chemotherapy for metastatic disease. The prostate contains organ-specific TAA that can serve as targets of an immune response. Because the prostate is not essential, its removal or destruction in many patients with CaP eliminates the concern for potential autoimmune disease. Moreover, immunotherapies can be directed at metastases without concern regarding the tissue of origin.

One immunotherapeutic approach for cancer involves the use of a patient's tumor cells mixed with various adjuvants, including cytokines, or genetically modified autologous cells that secrete cytokines. Hwang et al., *Semin Oncol.* 26:192-201 (1999). Among the drawbacks of whole cell vaccines is that it is labor-intensive and time consuming, especially if the cells are to be genetically modified. The success, or the lack of success, in the expansion of primary cultures for autologous vaccines can limit the courses of vaccinations and, further, an autologous vaccine needs to be specifically made for each patien. Simons et al., *Semin. Oncol.* 25:661-76 (1998). Another strategy for generating antigen-specific immunity is the ex vivo administration of specific antigen or peptides to antigen-presenting cells (APC). Again, this type of therapy is limited by the need to culture cells from each patient and success in the expansion of primary cultures for autologous vaccines can limit the number of courses of vaccination. Furthermore, the use of peptides to "load" APCs faces the obstacle of finding HLA-restricted peptides for all the different polymorphic HLA molecules. (Hwang et al., 1999).

The emergence of prostate cancer (CaP) as a major health issue and the absence of curative treatment for metastatic disease necessitate the development of new treatment modalities.

SUMMARY OF THE INVENTION

The present invention relates to the stimulation of specific cellular and humoral immune responses against prostate specific molecules in subjects vaccinated with recombinant bacille Calmette-Guérin (rBCG) bacterial strains expressing prostate specific molecules.

Novel compositions and methods are provided for eliciting immune responses against prostate specific antigens. The immune responses are useful for treating prostate cancer.

Prostate-specific antigen (PSA) and prostate specific membrane antigen (PSMA) are two prostate-specfic TAA. PSA is expressed almost exclusively in normal, benign, and malignant prostate cells. Circulating PSA levels are frequently elevated with primary, locally recurrent or metastatic prostate cancer. Carr et al., *Cancer Res.* 55:2455-62 (1995). PSMA is predominantly found in the prostate and is upregulated in primary and metastatic prostate cancer. Moreover, PSMA has been observed in endothelial cells of capillary beds in certain tumors including those of the prostate. Therefore, PSMA may be targeted in tumor neovasculature as well as in carcinoma cells. Maraj et al., *Br. J. Urol.* 81:523-8 (1998).

In one aspect of the invention, rBCG strains are provided that express PSA. In another aspect of the invention, rBCG strains are provided that express PSMA or fragment thereof. Two particularly useful fragments are the amino-terminal 437 amino acids and the carboxy-terminal 446 amino acids.

The invention also provides methods of eliciting useful immune responses, particularly cell mediated responses, against PSA, PSMA or a fragment thereof in a mammal.

The invention further provides methods of treating prostate cancer, both organ limited and metastatic, in a mammal by eliciting an immune response against PSA, PSMA, fragments thereof, or a combination of the foregoing.

DESCRIPTION OF THE FIGURES

FIG. 2 depicts expression of PSMA in BCG. Lane 1: positive control, lysate of influenza virus that has correct HA serotype (X-47E4940); Lane 2: negative control, lysate of influenza virus that has different HA serotype (PR8 E5201); Lane 3: lysate of BCG that expresses a control protein; Lanes 4 and 5: lysate of two clones of BCG2400 (clones 2400.2 and 2400.7, expressing full-length); Lane 6: lysate of BCG1300

(expressing amino-terminal 437 amino acids of PMSA); Lanes 7, 8, and 9: lysates of three clones of BCG1500 (clones 1500.2, 1500.7, and 1500.9, expressing carboxyl-terminal 446 amino acids of PMSA).

DETAILED DESCRIPTION OF THE INVENTION

The present invention is directed generally to vaccines and immunotherapeutics for treating prostate cancer. Specifically, the present invention is directed to presentation of prostate specific antigens to the host immune system to generate an immune response strong enough to have a therapeutic effect. The inventor has discovered that potent immune responses and successful therapy can be achieved by presentation of prostate specific proteins by an intracellular pathogen. That is, the vaccines and methods of the invention provide a means to sensitize the host immune system to that it will react with certain self antigens that are expressed in tumor tissue and neoplasms and cancers from tumor tissue.

Mycobacteria have adjuvant properties among the best currently known and stimulate a recipient's immune system to respond to other antigens with great effectiveness. A particularly valuable aspect of the vaccines produced with BCG is that cell-mediated immunity is elicited, which is especially useful in cases where cell-mediated immunity is considered to be critical for effective treatment, for example in treatment of neoplastic diseases. Although humoral responses also result, immune protection from mycobacterial infection has been shown to depend on the development of host type-1T-helper (Th1) cell mediated responses. rBCG can also be effective in stimulating cytotoxic T lymphocytes. To promote cell mediated responses, certain cytokines may also be used. For example, IL-2 and granulocyte-macrophage colony-stimulating factor amplify production of IFN-γ, which is characteristic of a Th1 response. Administration of IL-2 can result in stronger cellular responses to BCG and rBCG vaccines.

The experiments that follow demonstrate that immunization of mice with recombinant BCG expressing prostate-specific antigens induces readily detectable, specific, cell mediated delayed type hypersensitivity (DTH) responses to PSA and PSMA. For PSA and PSMA, the ability of rBCG to elicit a cell-mediated response is highly desirable. Notably, cellular, rather than humoral immune responses are responsible for the rejection of transplanted tumors or allogeneic tissue. Advantageously, mycobacteria also stimulates long-term memory or immunity, such that a single inoculation can be used to produce long-term sensitization to protein antigens.

Historically, BCG has been used as a vaccine for tuberculosis and has a very low incidence of adverse effects. Further, it can be used repeatedly in an individual (e.g., as the basis of vaccines that present different immunogens).

In one embodiment of the invention, recombinant BCG and vaccines therefrom contain a single prostate specific antigen, for example, PSA, PMSA, or fragments thereof. In another embodiment of the invention, different rBCG strains can be used to present multiple antigens.

Polypeptides can be expressed in BCG recombinants under the control of a mycobacterial stress responsive promoter—typically a hsp60 or hsp70 promoter. In the present case, prostate specific antigens are expressed under the control of the BCG hsp60 promoter, but other hsp promoters may be used.

Recently, vectors have become available that are capable of shuttling between *E. coli* and BCG. That and the discovery of high-efficiency heat-shock promoters that work in both types of bacteria has facilitated genetic manipulation of BCG strains. Generally, two types of vectors are available. Nonintegrating plasmids have the advantage of higher copy number, whereas integrating vectors provide stable expression in the absence of continued antibiotic selection. See, Stover et al., *Nature* 351:456-60 (1997). Either type of vector may be used according to the invention.

Although slow growing, having a generation time of 20-24 hours, BCG can readily be cultured by methods well known in the art. Accordingly, rBCG is easily prepared for storage and administration. Moreover, BCG vaccines can be prepared and freeze dried for reconstitution at the time of administration.

Recombinant BCG of the present invention can be administered by known methods. Vaccines can be administered using one or more routes, including, but not limited to, subcutaneous, intramuscular, intranasal, intraperitoneal, intradermal, oral, or inhalation. rBCG of the present invention survive within the recipient expressing and secreting prostate specific antigens in situ. They can be administered alone to produce a desired response, such as an immune response, or can be administered in combination with other agents in order to enhance or modify the resulting response.

In the methods of the present invention, a therapeutically effective amount of a recombinant BCG strain is administered. The term "administering" as used herein means delivering the antibodies of the present invention to a mammal by any method that may achieve the result sought. The term "mammal" as used herein is intended to include, but is not limited to, humans, laboratory animals, domestic pets and farm animals. "Therapeutically effective amount" means an amount of antibody of the present invention that, when administered to a mammal, is effective in producing the desired therapeutic effect. Desired therapeutic effects include, for example, tumor regression, or maintenance of responsiveness to test antigens. Various methods are available for monitoring immune responses. For example, individuals primed in vivo with exogenous or endogenous antigen have lymphocytes in their blood that maintain an immunological memory for the priming antigen. Stimulated of whole blood with a test antigen followed by the quantitative measurement of IFN-gamma in plasma can be used to measure an individual's cellular immune response.

In summary, rBCG expressing prostate-specific molecules provides an effective immunotherapy for prostate cancer and avoids the drawbacks of other treatment methadologies. BCG engenders a strong, long-lived immune response due to the ability to survive for several weeks in the host's macrophages, which can eliminate the need for numerous vaccine boosts. Live BCG is currently used as the vaccine for tuberculosis and its safety is already well established. This is beneficial due to the fact that live, antigen-expressing recombinant BCG appear to be critical for providing strong, specific, cell-mediated immunity; dead recombinant BCG and live non-recombinant BCG mixed with antigens are significantly less effective The experiments demonstrate that recombinant BCG strains are capable of eliciting an immune response against PSA and PSMA. Delayed type hypersensitivity was induced against both PSA and PSMA. A delayed antibody response to PSA in animals vaccinated with BCG-PSA is observed compared to vaccination with human PSA. Clinically, vaccines comprising recombinant BCG strains are particularly useful for stimulating an immune response against prostate molecules that can eradicate metastatic prostate cancer cells. The experiments show that recombinant BCG expressing prostate-specific antigens induces readily detectable, specific, cell mediated immune responses to PSA and PSMA, which can be used to eradicate undetected metastatic prostate cancer after radical prostatectomy.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed may be made by one skilled in the art and it is intended that such modifications are to be included within the scope of the present invention.

The examples which follow further illustrate the invention, but should not be construed to limit the scope in any way.

EXAMPLES

Gene Clones—A cDNA clone for PSA was provided by Dr. Tim Ratliff (Washington University, St. Louis, Mo.). A cDNA for PSMA was a gift from Drs. Warren Heston and Polly Gregor (Memorial Sloan-Kettering Cancer Center, New York, N.Y.). Sequences for the gene, mRNA, coding sequence, and complete protein are available from GenBank (PSA: Genbank Accession No. NM001648; PMSA: Genbank Accession No. AF007544).

Expression Vectors—pMM7 is a mycobacterial expression shuttle vector engineered to express and secrete foreign genes products in BCG. It was constructed by inserting the BCG alpha antigen signal sequence (AASS) between the heat shock protein (hsp) 60 promoter and the multicloning site of the pmv261 expression vector. O'Donnell et al., *Infect. Immun.* 62:2508-14 (1994). cDNAs of interest are inserted into the multicloning site of the vector and are constitutively expressed by the hsp 60 promoter. The AASS was inserted to allow for the possible secretion of protein products by the bacteria. Recombinant proteins produced by pMM7 are initially expressed as a fusion protein with the AASS, which is cleaved off during secretion. Recombinant BCG clones are selected in the presence of 50 µg per ml of kanamycin, the selectable marker on pMM7.

pMM7-HA is identical to pMM7 except for the insertion of an oligonucleotide tag (Flu+ GATCCAGCTTACCCATAC-GACGTCCCAGACTACGCTGCTACAG)(SEQ ID NO:5) coding for the influenza hemagglutinin (HA) sequence, YPY-DVPDYA (SEQ ID NO:6), between the AASS and the multicloning site.

Transformation of *E.coli*—The pMM7-PSA and pMM7-HA-PSMA plasmids were electroporated, separately, into XL1-Blue *E. coli*. Electroporation was performed using the BioRad Gene Pulser® Apparatus at the following settings: 25 uF, 2.5 kV, 200 ohms. After electroporation, 500 ul of warm SOC medium was added, and the cells were incubated for 30 minutes at 37° C. to allow for recovery and antibiotic resistance expression. The samples were plated separately onto L-broth agar plates (Life Technologies, Rockville, Md.) with 50 ug/ml kanamycin (Sigma, St. Louis, Mo.) and incubated overnight at 37° C. Kanamycin resistant colonies were picked and grown in 4 ml of L-Broth with 50 µg/ml kanamycin overnight at 37° C., with aeration. DNA was prepared using Qiagen miniprep extraction kits (Qiagen, Valencia Calif.) and clones were sequenced to ensure that the prostate specific cDNAs were in the correct reading frame.

Transformation of BCG—Constructs were electroporated, separately, into the Connaught strain of BCG, plated onto 7H10 Middlebrook agar (Difco, Detroit Mich.) containing 50 µg/ml kanamycin and incubated at 37° C. Kanamycin resistant colonies were picked after approximately 6 weeks and grown in 7H9 Middlebrook broth, containing 50 µg/ml kanamycin, at 37° C., with aeration (Difco, Detroit Mich.), until an $OD_{600}$ of approximately 1.0. BCG were harvested by centrifugation and washed 2 times with PBS containing 0.02% Tween-80 and disrupted by sonication with a Branson Sonifier (output control 7, duty cycle 50%, 4 minutes) in RIPA buffer containing a protease inhibitor cocktail composed of: 0.01 mg/ml Aprotinin, E-64, Leupeptin, and Pepstatin A, and 0.50 mg/ml Pefabloc in DMSO.

Western Blot Analysis BCG lysates were diluted 1:1 with 2× electrophoresis loading buffer (Sambrook et al., Molecular: Cloning, A Laboratory Manual, $2^{nd}$ Ed., Cold Spring Harbor Laboratory Press, 1989), boiled and size fractionated by SDS-PAGE using a Novex minigel apparatus (Novex, San Diego Calif.). BCG-PSA lysates were fractionated on 12% pre-cast Novex Tris-glycine gels and BCG-PSMA lysates were separated on 10% Novex NuPage gels. Fractionated proteins were transferred to Immobilon-P membrane (Millipore, Bedford, Mass.) using a BioRad Trans-Blot® SD apparatus at 12V for 45 minutes using 20 percent transfer buffer (Sambrook et al.) The membrane was blocked with 5% blocking solution (PBS containing 2.5% dry milk and 2.5% BSA) for 1 hour on a rotating platform, at room temperature, and rinsed once with PBS. The blot was then incubated, overnight, on a rotating platform at 4° C., with a 1:100 dilution of a mouse anti-PSA monoclonal antibody, ER-PR8 (Dako, Carpinteria, Calif.) or a 1:1000 dilution of anti-HA tag (Covance Richmond, Calif.) accordingly. The blot was washed 3 times with PBS containing 0.05% Tween, and once with PBS (10 minutes each) and incubated with horseradish peroxidase (HRP)-labeled, rat anti-mouse $IgG_1$ antibody (1:1000 dilution; PharMingen, San Diego Calif.) for 45 minutes at room temperature, and washed as above. A 1:1 mixture of the ECL Western Blot Systems (Amersham Pharmacia Biotech, Piscataway N.J.) solutions was applied to the blot for 1 minute with vigorous shaking. Excess moisture was removed and X-ray film (Marsh Biomedical Products, Rochester, N.Y.) was exposed to the blot in a dark room for 5 minutes then processed by a Kodak M35A X-OMAT Processor (Rochester, N.Y.). Human PSA (Scripps Laboratories, San Diego, Calif.), influenza virus (gift from Dr. Edwin Kilborne, New York Medical College, Valhalla, N.Y.) and HA tagged molecular weight markers (Roche Pharmaceuticals, Indianapolis Ind.) were used as standards and/or positive controls.

The densitometry used to calculate the protein concentration on autoradiographs was performed using an Alpha Imager™ 2000, IS-1000 Digital Imaging System (Alpha Innotech Corp., San Leandro, Calif.).

Figure 1:
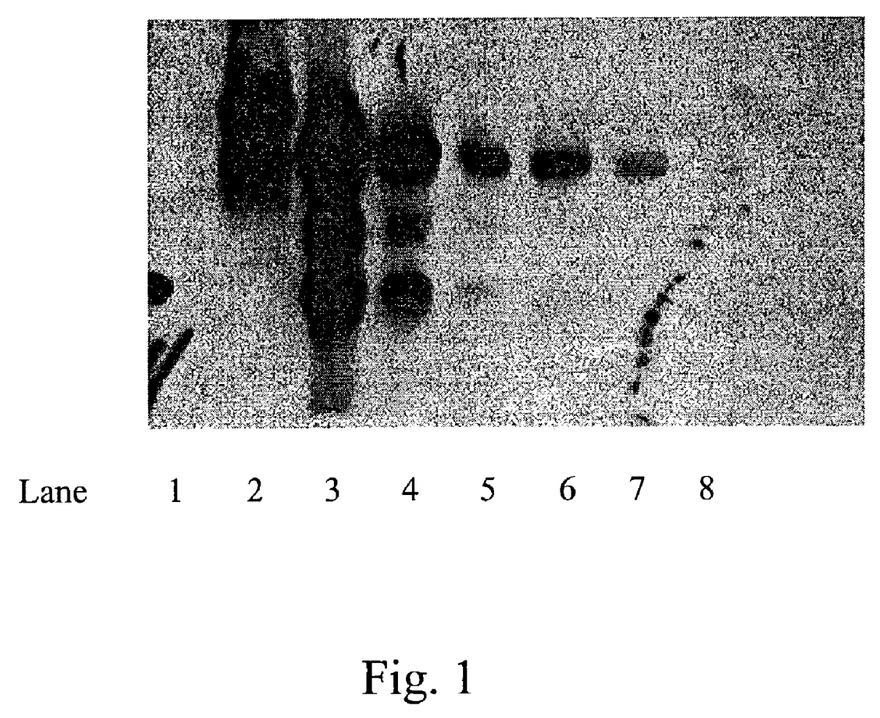
FIG. 1 depicts the quantitation of PSA in the BCG-PSA4 clone. Lane 1: negative control, lysate of BCG that expresses a control protein; Lane 2: lysate of BCG-PSA4; Lanes 3-8: two fold serial dilutions (200-6.25 ng) of human PSA (~32 kD, plus smaller breakdown products).

Cloning and Expression of PSA and PSMA.—The entire coding region of PSA was cloned into the Pst I/Hind III restriction sites of pMM7. Following electroporation into BCG, two clones were identified that expressed PSA. Western blot analysis followed by densitometry, using known amounts of purified human PSA as standards, was used to quantitate PSA expression. The lysate from clone BCG-PSA4 contained approximately 24 ng of PSA per microgram of BCG protein (FIG. 1).

Figure 2:
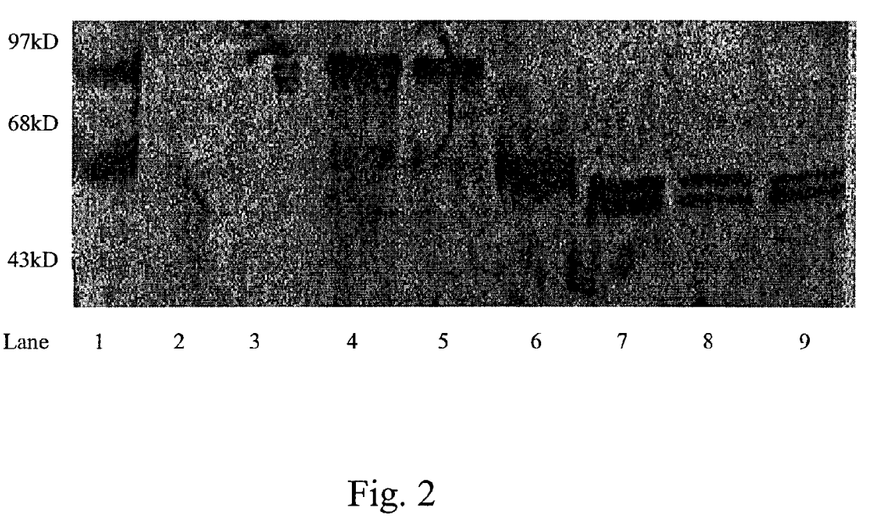

The entire coding region of PSMA was cloned into the Pvu II restriction enzyme site of pMM7-HA. Following electroporation into BCG, two clones were identified that expressed PSMA. As depicted in FIG. 2, PSMA is detected as an approximately 86 kD band. As PSMA is a large protein (750 amino acids) it was anticipated that it may not be efficiently expressed in BCG. Therefore, two overlapping fragments of PSMA were individually cloned into pMM7-HA. One fragment contains the 5-prime 1314 nucleotides (encoding the amino-terminal 437 amino acids of PSMA; clone BCG-PSMA1300). The second fragment contains the 3-prime 1483 nucleotides of PSMA (encoding the 446 carboxyl-terminal amino acids of PSMA; clone BCG-PSMA1500). Both of these fragments are efficiently expressed in BCG (FIG. 2; BCG-PSMA1300: 0.66 ng PSMA/μg of BCG protein; BCG-PSMA1500: 0.47 ng PSMA/μg of BCG protein).

PSMA expression in lysates was quantitated using serial dilutions of a known 30 kD HA tagged molecular weight marker on Western Blot analysis, followed by densitometry. The lysate of BCG-PSMA2400.2 contained approximately 112 pg of PSMA/μg of BCG protein. Clone BCG-PSMA2400.7 has approximately 370 pg of PSMA/μg of BCG protein.

Immunization of mice—Six to ten week old (C57BL/6× BALB/c) F1 (CBF1) mice were obtained from Jackson Laboratories (Bar Harbor, Me.). CBF1 mice were subcutaneously injected with one million colony-forming units of rBCG-PSA, rBCG-PSMA1300 (expressing the 5'-1314 nucleotides encoding the amino terminal 438 amino acids of PSMA), BCG (with vector only), 5 μg of PSA protein, 5 μg of PSMA protein or PBS (100 μl total volume).

Detection of DTH—Groups of 5 immunized and control mice were challenged 12 weeks after vaccination with 10 μg PSA or 5 μg PSMA in 10 μl of PBS into the footpad using 100 μl Hamilton syringe fitted with a 30 or 26 gauge needle. Footpad thickness was measured by a vernier caliper, prior to and 24 and 48 hours after challenge. The mice were then sacrificed and the hind paws were removed, fixed in formalin, embedded in paraffin, and coded hematoxylin and eosin sections were evaluated for mononuclear cell infiltrates. Sections were scored as 0 (no infiltrates) to 5 (extensive infiltrates and necrosis), and scores were averaged. Differences in footpad thickness and differences in mean infiltrate intensity analyzed statistically by one-way analysis of variance (ANOVA) with a Tukey-Kramer multiple-comparison post-test. Coded sections were also stained for non-specific esterase (NSE, Sigma Chemical Co., St. Louis, Mo.) according to the manufacturer's instructions for evaluation of macrophage infiltrates. Results are reported as per cent macrophages per hundred infiltrating mononuclear cells.

Figure 3:
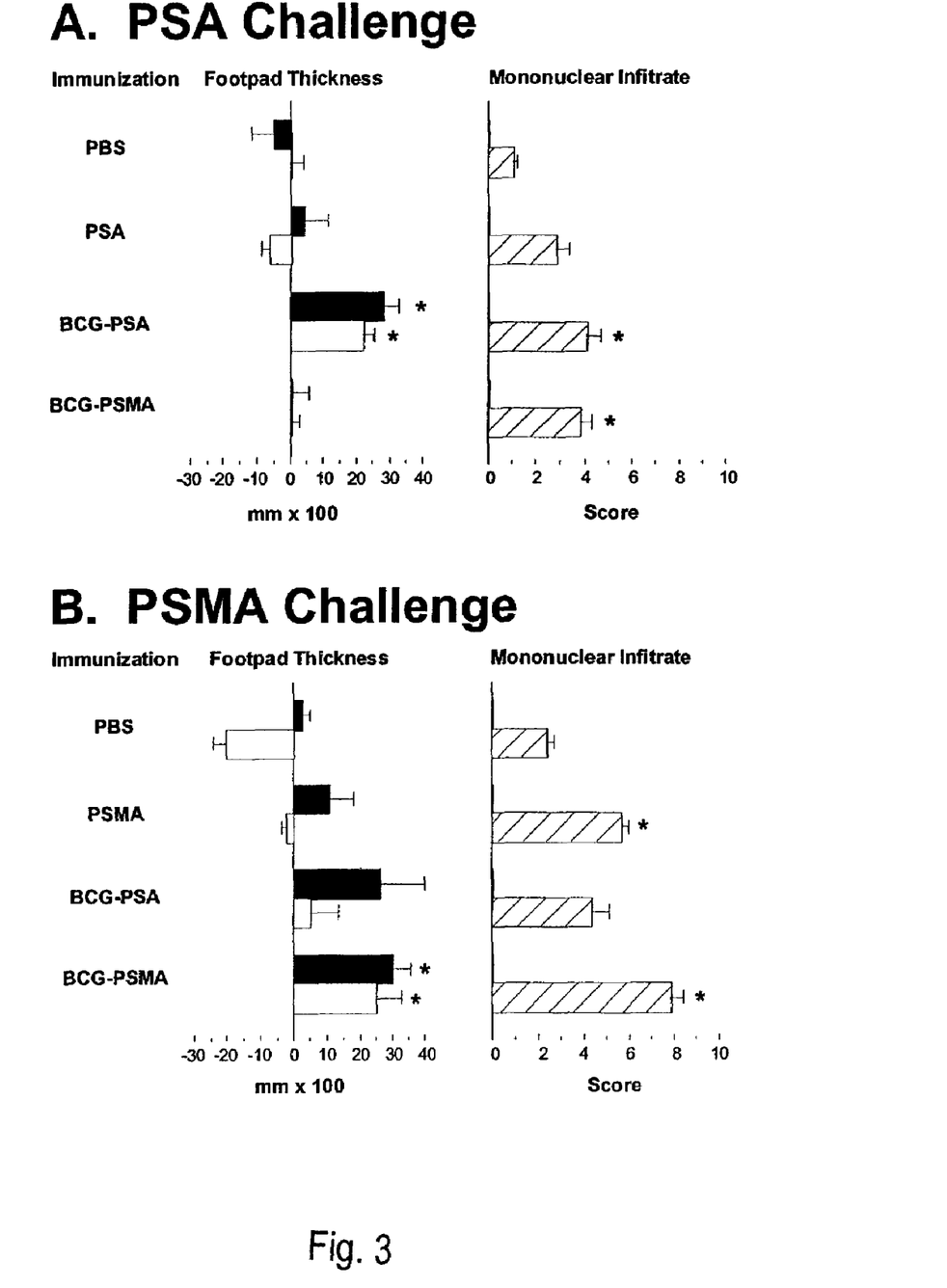
FIG. 3 depicts the delayed type hypersensitivity (DTH) response in mice immunized with rBCG. Mice were challenged with either soluble PSA (Panel A) or PSMA (Panel B) and the response was quantified by increased footpad thickness (black bars: 24 hours; white bars: 48 hours) and histologic evaluation of infiltrates (white hatched bars) at 48 hours.
Figure 4:
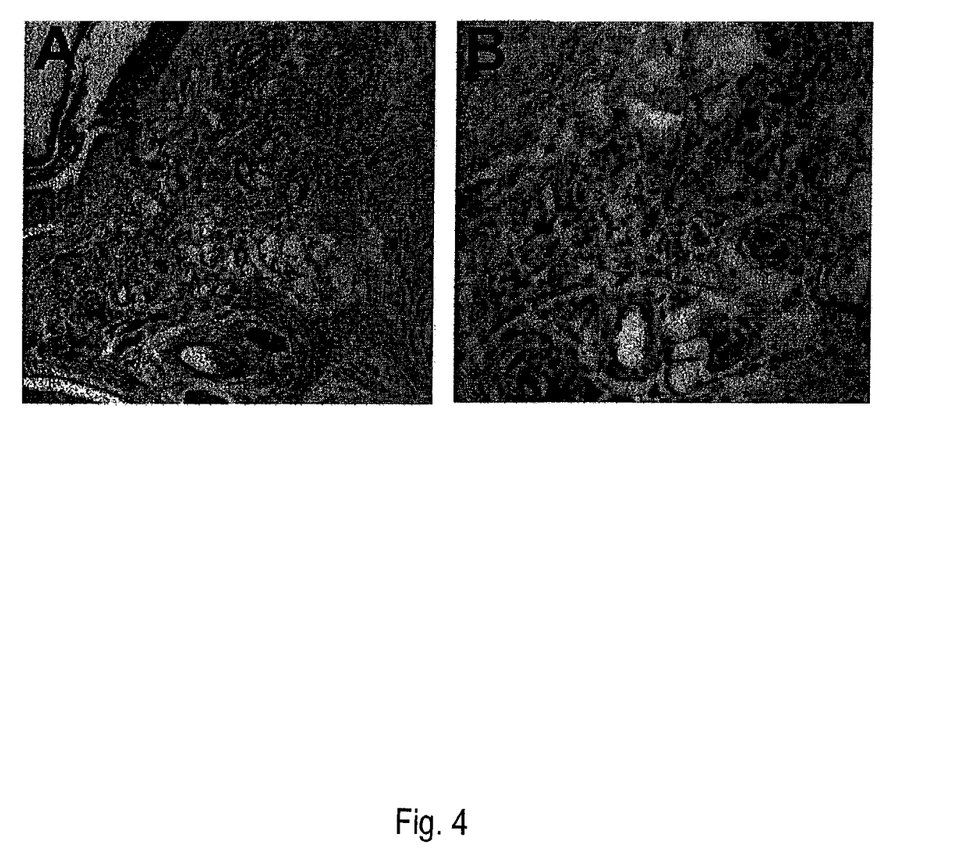
FIG. 4 depicts the analysis of DTH reactions in mouse footpads 48 hours after elicitation by PSMA in a mouse vaccinated with rBCG-PSMA 12 weeks earlier. Mononuclear cell dermal infiltrates (arrowheads) are identifiable at 100× (FIG. 4A) and at 400× (FIG. 4B) magnification (hematoxylin and eosin).

BCG-PSA and BCG-PMSA induced specific DTH as measured by increases in footpad thickness that were maximal at 24 h which could only be elicited by the homologous protein antigen. Thus, only mice immunized with BCG expressing PSA exhibited a significant increase in footpad thickness in response to challenge by the PSA protein (FIG. 3A). Similarly, only mice immunized with BCG expressing PMSA exhibited a significant increase in footpad thickness in response to challenge with PMSA protein (FIG. 3B). PSA protein elicited significantly more intense mononuclear cell infiltrates at 48 h in animals immunized with rBCG-PSA or with rBCG-PMSA than in animals immunized with PSA or PBS ($P<0.01$, FIG. 3B). PMSA elicited significantly more mononuclear cell infiltrates at 48 h in animals immunized with PSMA or with rBCG-PMSA than in animals immunized with BCG-PSA or PBS ($P<0.01$, FIG. 3B). An example of the mononuclear cell infiltrates seen in these reactions is shown in FIG. 4. Forty-five percent of the infiltrating cells were esterase-positive macrophages (data not shown). No neutrophil infiltrates were observed in any section. PMSA protein elicited some mononuclear infiltrates even in animals immunized with PBS (FIG. 3B). This may be due to the solubilization of PSMA in urea which would have contributed to the presence of inflammatory cells at the site of injection resulting in a microscopic response in the absence of measurable foot pad swelling. Nevertheless, our data suggest that immunization with rBCG that express prostate specific molecules can stimulate cellular immune responses against the recombinant proteins.

Detection of an Antibody Response—Individual samples of serum were collected from each mouse by retro-orbital bleeding prior to, and 5 and 10 weeks after immunization. Equal amounts of sample from animals in each group were pooled. ELISA was used to assay anti-PSA and PSMA antibodies. Ninety six-well lmmunlon-2 plates were coated with 100 ng/well of PSA in 100 μl of coating buffer (0.1 M $NaHCO_3$ pH 9.6), and incubated overnight at 37° C. after which the excess liquid was decanted. One hundred micrograms of PSMA solubilized in 8M urea or PSA was coated onto wells and incubated overnight at 4° C. after which the excess liquid was decanted, the plate was rinsed once with PBS, and blocked with 200 μl of 5% BSA in PBS per well for 1 hour at room temperature. To measure antibody activity, samples (100 μl) diluted in 1% BSA-0.05% Tween 20-PBS were then added to wells and incubated for 1 hour at room temperature. Preimmune sera were diluted 1:20, post-immune sera were serially diluted 2-fold (1:20 to 1:2560). The plate was then washed 5 times with 0.05% Tween-20 in PBS and once with PBS, and 100 μl HRP-conjugated rabbit anti-mouse IgG (H+L) (Jackson ImmunoResearch Laboratories, West Grove, Pa.) diluted 1:1000 in 1% BSA-0.05% Tween-20-PBS was added. After a 1 hour incubation at room temperature, the plate was washed as above, and colorimetric analysis was performed using TMB Microwell Peroxidase Substrate System (Kirkegaard and Perry Laboratories, Inc., Gaithersburg, Md.). Antibody titers were defined as the reciprocal of the highest dilution at which the values of absorbance at 450 nm ($A_{450}$) were 2 standard deviations greater than those obtained with pre-immune sera diluted 1:20.

Figure 5:
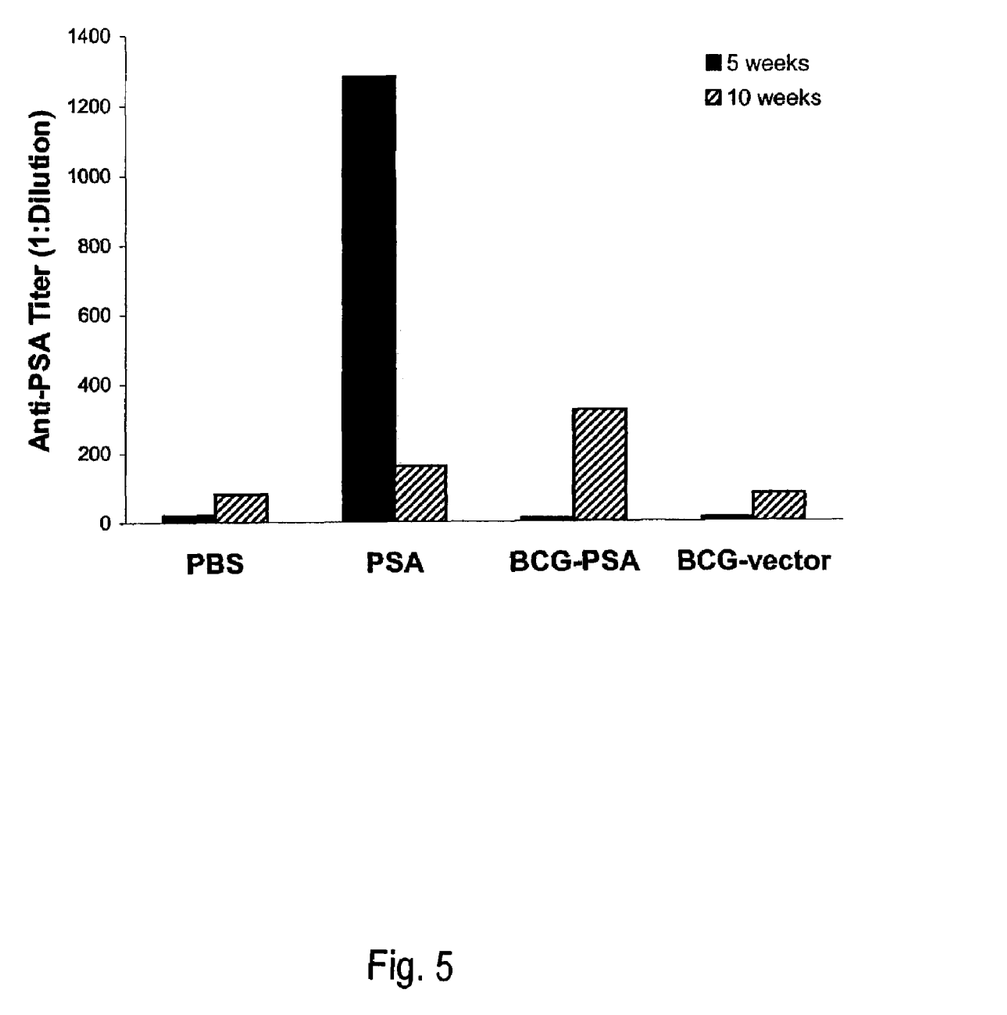
FIG. 5 depicts the antibody response to PSA in mice at 5 (hatched bars) and 10 (solid bars) weeks after immunization with PBS, PSA, rBCG-PSA or rBCG-PSMA1300. Sera not showing a response at the lowest dilution tested, 1:10, were assigned a titer of 10.

Mice immunized with rBCG-PSA generated a weak antibody response to PSA, which became detectable (titer=320) at week 10. Mice immunized with human PSA had a high antibody titer (1250) at 5 weeks which decreased significantly (160) by week 10 (FIG. 5). Immunization with BCG containing only vector or with PBS did not stimulate an anti-PSA antibody response. Similar results were obtained in a second duplicate experiment (data not shown).

The ingredients and method steps should be understood as examples that are intended to be illustrative only. In particular, the invention is not intended to be limited to the methods, protocols, conditions and the like specifically recited herein, insofar as those skilled in the art would be able to substitute other conditions, methods, amounts, materials, etc. based on the present disclosure to arrive at compounds within the scope of this disclosure. While the present invention is described with respect to particular examples and preferred embodiments, the present invention is not limited to these examples and embodiments. In particular, the compounds of the present invention are not limited to the exemplary species recited herein.

What is claimed is:

1. A recombinant bacille Calmette-Guérin (rBCG) strain that comprises an expressible polynucleotide that encodes an amino-terminal prostate specific membrane antigen (PSMA) fragment consisting of the amino acid sequence of SEQ ID NO:4 from amino acid 1 to amino acid 437.

2. The recombinant bacille Calmette-Guérin strain of claim 1, that expresses the amino-terminal prostate specific membrane antigen (PSMA) fragment.

3. The recombinant bacille Calmette-Guérin strain of claim 1, wherein the expressible polynucleotide further encodes a secretion signal sequence.

4. The recombinant bacille Calmette-Guérin strain of claim 3, wherein the secretion signal sequence is the bacille Calmette-Guérin alpha antigen signal sequence (AASS).

5. The recombinant bacille Calmette-Guérin strain of claim 1, wherein the expressible polynucleotide further encodes an oligonucleotide tag encoding an influenza hemagglutinin polypeptide.

6. The recombinant bacille Calmette-Guérin strain of claim 5, wherein the influenza hemagglutinin polypeptide has the amino acid sequence of SEQ ID NO:6.

7. The recombinant bacille Calmette-Guérin strain of claim 1, wherein the expressible polynucleotide is in a mycobacterial shuttle vector.

8. The recombinant bacille Calmette-Guérin strain of claim 7, wherein the shuttle vector is pMM7-HA.

9. A recombinant bacille Calmette-Guérin (rBCG) strain which comprises an expressible polynucleotide that encodes an amino-terminal prostate specific membrane antigen (PSMA) fragment, wherein the expressible polynucleotide consists of the nucleotide sequence of SEQ ID NO:3 from nucleotide 259 to nucleotide 1572.

10. The recombinant bacille Calmette-Guérin strain of claim 9, wherein the expressible polynucleotide further encodes a secretion signal sequence.

11. The recombinant bacille Calmette-Guérin strain of claim 10, wherein the secretion signal sequence is the bacille Calmette-Guérin alpha antigen signal sequence (AASS).

12. The recombinant bacille Calmette-Guérin strain of claim 9, wherein the expressible polynucleotide further encodes an oligonucleotide tag encoding an influenza hemagglutinin polypeptide.

13. The recombinant bacille Calmette-Guérin strain of claim 12, wherein the influenza hemagglutinin polypeptide has the amino acid sequence of SEQ ID NO:6.

14. A recombinant bacille Calmette-Guérin (rBCG) strain which comprises an expressible polynucleotide that encodes an amino-terminal prostate specific membrane antigen (PSMA), wherein the expressible polynucleotide consists of the nucleotide sequence of SEQ ID NO:3 from nucleotide 259 to nucleotide 1572, a bacille Calmette-Guérin alpha antigen signal sequence (AASS), and an influenza hemagglutinin polypeptide tag having the amino acid sequence of SEQ ID NO:6.

15. The recombinant bacille Calmette-Guérin(rBCG) strain of claim 9 or 14, wherein the expressible polynucleotide is in a mycobacterial shuttle vector.

16. The recombinant bacille Calmette-Guérin strain of claim 15, wherein the shuttle vector is pMM7-HA.

* * * * *

```
                        SEQUENCE LISTING

<160> NUMBER OF SEQ ID NOS: 6

<210> SEQ ID NO 1
<211> LENGTH: 1464
<212> TYPE: DNA
<213> ORGANISM: human
<220> FEATURE:
<223> OTHER INFORMATION: PSA mRNA
<220> FEATURE:
<221> NAME/KEY: CDS
<222> LOCATION: (42)...(827)
<300> PUBLICATION INFORMATION:
<308> DATABASE ACCESSION NUMBER: GenBank Accession No. NM_001648
<309> DATABASE ENTRY DATE: 2003-10-04

<400> SEQUENCE: 1
agccccaagc ttaccacctg cacccggaga gctgtgtcac catgtgggtc ccggttgtct      60
tcctcaccct gtccgtgacg tggattggtg ctgcacccct catcctgtct cggattgtgg     120
gaggctggga gtgcgagaag cattcccaac cctggcaggt gcttgtggcc tctcgtggca     180
gggcagtctg cggcggtgtt ctggtgcacc cccagtgggt cctcacagct gcccactgca     240
tcaggaacaa aagcgtgatc ttgctgggtc ggcacagcct gtttcatcct gaagacacag     300
gccaggtatt tcaggtcagc cacagcttcc cacacccgct ctacgatatg agcctcctga     360
agaatcgatt cctcaggcca ggtgatgact ccagccacga cctcatgctg ctccgcctgt     420
cagagcctgc cgagctcacg gatgctgtga aggtcatgga cctgcccacc caggagccag     480
cactggggac cacctgctac gcctcaggct ggggcagcat tgaaccagag gagttcttga     540
ccccaaagaa acttcagtgt gtggacctcc atgttatttc caatgacgtg tgtgcgcaag     600
ttcaccctca gaaggtgacc aagttcatgc tgtgtgctgg acgctggaca gggggcaaaa     660
gcacctgctc gggtgattct ggggccccac ttgtctgtaa tggtgtgctt caaggtatca     720
cgtcatgggg cagtgaacca tgtgccctgc ccgaaaggcc ttccctgtac accaaggtgg     780
tgcattaccg gaagtggatc aaggacacca tcgtggccaa cccctgagca ccctatcaa      840 cccctattg tagtaaactt ggaaccttgg aaatgaccag gccaagactc aagcctcccc     900
agttctactg acctttgtcc ttaggtgtga ggtccagggt tgctaggaaa agaaatcagc     960
agacacaggt gtagaccaga gtgtttctta aatggtgtaa ttttgtcctc tctgtgtcct    1020
ggggaatact ggccatgcct ggagacatat cactcaattt ctctgaggac acagatagga    1080
tggggtgtct gtgttatttg tggggtacag agatgaaaga ggggtgggat ccacactgag    1140
agagtggaga gtgacatgtg ctggacactg tccatgaagc actgagcaga agctggaggc    1200
acaacgcacc agacactcac agcaaggatg gagctgaaaa cataacccac tctgtcctgg    1260
aggcactggg aagcctagag aaggctgtga gccaaggagg gagggtcttc ctttggcatg    1320
ggatggggat gaagtaagga gagggactgg accccctgga agctgattca ctatgggggg    1380
aggtgtattg aagtcctcca gacaaccctc agatttgatg atttcctagt agaactcaca    1440
gaaataaaga gctgttatac tgtg                                           1464

<210> SEQ ID NO 2
<211> LENGTH: 261
<212> TYPE: PRT
```

```
<213> ORGANISM: human
<220> FEATURE:
<223> OTHER INFORMATION: PSA
<300> PUBLICATION INFORMATION:
<308> DATABASE ACCESSION NUMBER: GenBank Accession No. NM_001648
<309> DATABASE ENTRY DATE: 2003-10-04

<400> SEQUENCE: 2
```

Met Trp Val Pro Val Val Phe Leu Thr Leu Ser Val Thr Trp Ile Gly
              5                   10                  15

Ala Ala Pro Leu Ile Leu Ser Arg Ile Val Gly Gly Trp Glu Cys Glu
             20                  25                  30

Lys His Ser Gln Pro Trp Gln Val Leu Val Ala Ser Arg Gly Arg Ala
             35                  40                  45

Val Cys Gly Gly Val Leu Val His Pro Gln Trp Val Leu Thr Ala Ala
          50                  55                  60

His Cys Ile Arg Asn Lys Ser Val Ile Leu Leu Gly Arg His Ser Leu
 65                  70                  75                  80

Phe His Pro Glu Asp Thr Gly Gln Val Phe Gln Val Ser His Ser Phe
                 85                  90                  95

Pro His Pro Leu Tyr Asp Met Ser Leu Leu Lys Asn Arg Phe Leu Arg
                100                 105                 110

Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
        130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
                180                 185                 190

Thr Lys Phe Met Leu Cys Ala Gly Arg Trp Thr Gly Gly Lys Ser Thr
            195                 200                 205

Cys Ser Gly Asp Ser Gly Gly Pro Leu Val Cys Asn Gly Val Leu Gln
        210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

```
<210> SEQ ID NO 3
<211> LENGTH: 2631
<212> TYPE: DNA
<213> ORGANISM: human
<220> FEATURE:
<223> OTHER INFORMATION: PSMA mRNA
<220> FEATURE:
<221> NAME/KEY: CDS
<222> LOCATION: (259)...(2511)
<300> PUBLICATION INFORMATION:
<308> DATABASE ACCESSION NUMBER: GenBank Accession No. AF007544
<309> DATABASE ENTRY DATE: 1998-12-10

<400> SEQUENCE: 3
```
aaaaggggcc ggatttcctt ctcctggagg cagatgttgc ctctctctct cgctcggatt      60
ggttcagtgc actctagaaa cactgctgtg gtggagaaac tggaccccag gtctggagcg     120

-continued

```
aattccagcc tgcagggctg ataagcgagg cattagtgag attgagagag actttacccc    180
gccgtggtgg ttggagggcg cgcagtagag cagcagcaca ggcgcgggtc ccgggaggcc    240
ggctctgctc gcgccgagat gtggaatctc cttcacgaaa ccgactcggc tgtggccacc    300
gcgcgccgcc cgcgctggct gtgcgctggg gcgctggtgc tggcgggtgg cttctttctc    360
ctcggcttcc tcttcgggtg gtttataaaa tcctccaatg aagctactaa cattactcca    420
aagcataata tgaaagcatt tttggatgaa ttgaaagctg agaacatcaa gaagttctta    480
cataatttta cacagatacc acatttagca ggaacagaac aaaactttca gcttgcaaag    540
caaattcaat cccagtggaa agaatttggc ctggattctg ttgagctagc tcattatgat    600
gtcctgttgt cctacccaaa taagactcat cccaactaca tctcaataat taatgaagat    660
ggaaatgaga ttttcaacac atcattattt gaaccacctc ctccaggata tgaaaatgtt    720
tcggatattg taccaccttt cagtgctttc tctcctcaag gaatgccaga gggcgatcta    780
gtgtatgtta actatgcacg aactgaagac ttctttaaat tggaacggga catgaaaatc    840
aattgctctg ggaaaattgt aattgccaga tatgggaaag ttttcagagg aaataaggtt    900
aaaaatgccc agctggcagg ggccaaagga gtcattctct actccgaccc tgctgactac    960
tttgctcctg gggtgaagtc ctatccagac ggttggaatc ttcctggagg tggtgtccag   1020
cgtggaaata tcctaaatct gaatggtgca ggagaccctc tcacaccagg ttacccagca   1080
aatgaatatg cttataggcg tggaattgca gaggctgttg gtcttccaag tattcctgtt   1140
catccaattg gatactatga tgcacagaag ctcctagaaa aaatgggtgg ctcagcacca   1200
ccagatagca gctggagagg aagtctcaaa gtgccctaca atgttggacc tggctttact   1260
ggaaactttt ctacacaaaa agtcaagatg cacatccact ctaccaatga agtgacgaga   1320
atttacaatg tgataggtac tctcagagga gcagtggaac cagacagata tgtcattctg   1380
ggaggtcacc gggactcatg ggtgtttggt ggtattgacc ctcagagtgg agcagctgtt   1440
gttcatgaaa ttgtgaggag ctttggaaca ctgaaaaagg aagggtggag acctagaaga   1500
acaatttttgt ttgcaagctg ggatgcagaa gaatttggtc ttcttggttc tactgagtgg   1560
gcagaggaga attcaagact ccttcaagag cgtggcgtgg cttatattaa tgctgactca   1620
tctatagaag gaaactacac tctgagagtt gattgtacac cgctgatgta cagcttggta   1680
cacaacctaa caaaagagct gaaaagccct gatgaaggct tgaaggcaa atctctttat   1740
gaaagttgga ctaaaaaaag tccttcccca gagttcagtg gcatgcccag gataagcaaa   1800
ttgggatctg gaaatgattt tgaggtgttc ttccaacgac ttggaattgc ttcaggcaga   1860
gcacggtata ctaaaaattg ggaaacaaac aaattcagcg gctatccact gtatcacagt   1920
gtctatgaaa catatgagtt ggtggaaaag ttttatgatc caatgtttaa atatcacctc   1980
actgtggccc aggttcgagg agggatggtg tttgagctag ccaattccat agtgctccct   2040
tttgattgtc gagattatgc tgtagtttta agaaagtatg ctgacaaaat ctacagtatt   2100
tctatgaaac atccacagga aatgaagaca tacagtgtat catttgattc acttttttct   2160
gcagtaaaga attttacaga aattgcttcc aagttcagtg agagactcca ggactttgac   2220
aaaagcaacc caatagtatt aagaatgatg aatgatcaac tcatgttttct ggaaagagca   2280
tttattgatc cattagggtt accagacagg cctttttata ggcatgtcat ctatgctcca   2340
agcagccaca acaagtatgc aggggagtca ttcccaggaa tttatgatgc tctgtttgat   2400
attgaaagca agtggaccc ttccaaggcc tggggagaag tgaagagaca gatttatgtt   2460
```

-continued

```
gcagccttca cagtgcaggc agctgcagag actttgagtg aagtagccta agaggatttt    2520
ttagagaatc cgtattgaat ttgtgtggta tgtcactcag aaagaatcgt aatgggtata    2580
ttgataaatt ttaaaattgg tatatttgaa ataaagttga atattatata t             2631
```

```
<210> SEQ ID NO 4
<211> LENGTH: 750
<212> TYPE: PRT
<213> ORGANISM: human
<220> FEATURE:
<223> OTHER INFORMATION: PSMA
<300> PUBLICATION INFORMATION:
<308> DATABASE ACCESSION NUMBER: GenBank Accession No. AF007544
<309> DATABASE ENTRY DATE: 1998-12-10

<400> SEQUENCE: 4
```

```
Met Trp Asn Leu Leu His Glu Thr Asp Ser Ala Val Ala Thr Ala Arg
                  5                  10                  15

Arg Pro Arg Trp Leu Cys Ala Gly Ala Leu Val Leu Ala Gly Gly Phe
             20                  25                  30

Phe Leu Leu Gly Phe Leu Phe Gly Trp Phe Ile Lys Ser Ser Asn Glu
         35                  40                  45

Ala Thr Asn Ile Thr Pro Lys His Asn Met Lys Ala Phe Leu Asp Glu
     50                  55                  60

Leu Lys Ala Glu Asn Ile Lys Lys Phe Leu His Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320
```

-continued

```
Gly Ser Leu Lys Val Pro Tyr Asn Val Gly Pro Phe Thr Gly Asn
            325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
            355                 360                 365

Asp Arg Tyr Val Ile Leu Gly Gly His Arg Asp Ser Trp Val Phe Gly
            370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                    405                 410                 415

Leu Phe Ala Ser Trp Asp Ala Glu Glu Phe Gly Leu Leu Gly Ser Thr
                    420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
            450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                    485                 490                 495

Trp Thr Lys Lys Ser Pro Ser Pro Glu Phe Ser Gly Met Pro Arg Ile
                    500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                    565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                    645                 650                 655

Asn Pro Ile Val Leu Arg Met Met Asn Asp Gln Leu Met Phe Leu Glu
                    660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                    725                 730                 735

Phe Thr Val Gln Ala Ala Ala Glu Thr Leu Ser Glu Val Ala
```

-continued

```
                740                 745                 750

<210> SEQ ID NO 5
<211> LENGTH: 43
<212> TYPE: DNA
<213> ORGANISM: artificial sequence
<220> FEATURE:
<223> OTHER INFORMATION: hemagglutinin tag

<400> SEQUENCE: 5
gatccagctt acccatacga cgtcccagac tacgctgcta cag                          43

<210> SEQ ID NO 6
<211> LENGTH: 9
<212> TYPE: PRT
<213> ORGANISM: artificial sequence
<220> FEATURE:
<223> OTHER INFORMATION: hemagglutinin tag

<400> SEQUENCE: 6

Tyr Pro Tyr Asp Val Pro Asp Tyr Ala
                 5
```